US00PP26588P2

(12) United States Plant Patent
Hansen

(10) Patent No.: US PP26,588 P2
(45) Date of Patent: Apr. 5, 2016

(54) ***BAPTISIA* PLANT NAMED 'PINK TRUFFLES'**

(50) Latin Name: ***Baptisia* hybrid**
Varietal Denomination: Pink Truffles

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 162 days.

(21) Appl. No.: 14/120,591

(22) Filed: Jun. 6, 2014

(51) Int. Cl.
*A01H 5/02* (2006.01)

(52) U.S. Cl.
USPC ..... Plt./263.1

(58) Field of Classification Search
USPC ..... Plt./263.1
CPC ..... A01H 5/02
See application file for complete search history.

*Primary Examiner* — Kent L Bell

(57) ABSTRACT

A new and distinct plant cultivar of hardy herbaceous False Indigo named *Baptisia* 'Pink Truffles' characterized by pinkish lavender flowers with exposed yellow keel petals on tall branched spikes just above the foliage in late spring, on upright, vase-shaped, multi-stemmed, winter-hardy plants with medium-green tri-foliate foliage, suitable for landscaping as a specimen or en masse.

1 Drawing Sheet

Botanical classification: *Baptisia* hybrid.
Cultivar designation: 'Pink Truffles'.

BACKGROUND OF THE INVENTION

The present invention relates to a new and distinct cultivar of hybrid *Baptisia* plant, botanically known as *Baptisia* 'Pink Truffles' and will be referred to hereafter by its cultivar name, 'Pink Truffles'. The new cultivar represents a new false indigo, a hardy herbaceous perennial grown for landscape and cut flower use.

The new invention arose from an ongoing breeding program at a nursery in Waseca, Minn. and continued at a wholesale perennial nursery in Zeeland, Mich. with the specific intention of improving garden worthiness of perennial False Indigo plants with a wider variety of flower colors and improved garden habit.

*Baptisia* 'Pink Truffles' was a selection of a proprietary hybrid given the breeder code name of 'Red Riding Hood' (not patented) and the male or pollen parent was an unknown *Baptisia* from an open pollinated isolation block selection consisting of proprietary complex hybrids. Also in the isolation block were advanced hybrids of *Baptisia minor, sphaerocarpa, alba,* and *cinerea.*

Seeds were collected from 'Red Riding Hood' individual selected female plants in fall of 2009 at the isolation block in Waseca, Minn., USA by the inventor. The exact identity of the male parent is not known but it was from proprietary unreleased and non-patented hybrid plants. The seeds were sown by the inventor in Zeeland, Mich., USA in the Fall of 2009 with the initial selection made in the spring of 2012 at a wholesale perennial nursery in Zeeland, Mich. The single seedling selected from the seed parent was assigned the breeder code of H9-51-01. Asexual propagation by cuttings was initially propagated in spring 2012. Sterile plant tissue culture can also be used for asexual propagation. The results of asexual propagation are that the new plant is stable and retains its true characteristics though successive generations of asexual propagation. Propagation method for asexually reproducing plants is primarily stem cuttings.

The nearest comparison plant is a proprietary unreleased hybrid assigned the breeder name of 'Penny's Tall Pink'. The new plant has a taller, more upright vase habit with thicker stiffer stems and clearer pinkish lavender flower compared to the rounded, shorter habit and more gray-brown tinted flowers. Another proprietary plant named just "pink *minor*" has a very rounded habit with lighter pink flowers on fewer stems with less coverage. These are the nearest comparison plants known to the inventor and *Baptisia* 'Pink Truffles' is distinct from these and all other *Baptisia* plants known to the inventor.

The new plant differs from all *Baptisia* known to the inventor in the following combined traits:

1. Pinkish lavender flowers with exposed yellow keel petals on tall branched spikes just above the foliage in late spring.
2. Upright, vase-shaped, multi-stemmed, winter-hardy habit.
3. Glaucous, medium-green, tri-foliate foliage.

BREF DESCRIPTION OF THE DRAWINGS

The photographs of the new plant demonstrate the unique traits of the new plant and the overall appearance. The colors are as accurate as reasonably possible with color reproductions. Variation in ambient light spectrum, source and direction may cause the appearance of minor variation in color. The accompanying photograph is of a three-year old plant growing in an open full-sun trial garden in Zeeland, Mich.

DETAILED BOTANICAL DESCRIPTION OF THE PLANT

Figure 1:
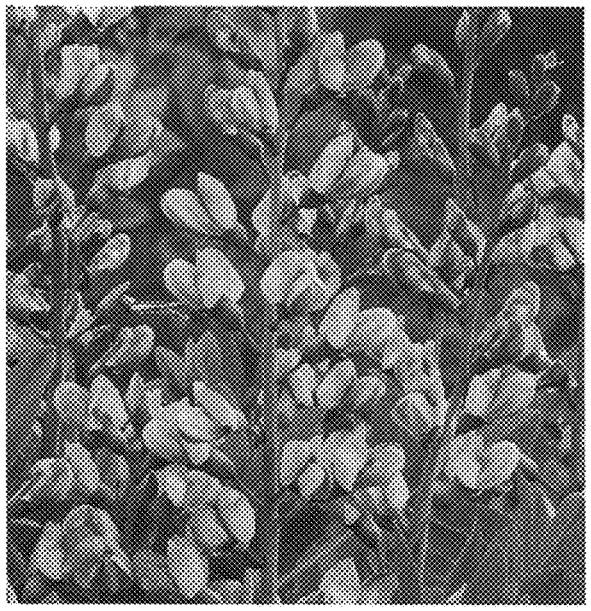
FIG. 1 shows a close-up of the flower scape.
Figure 2:
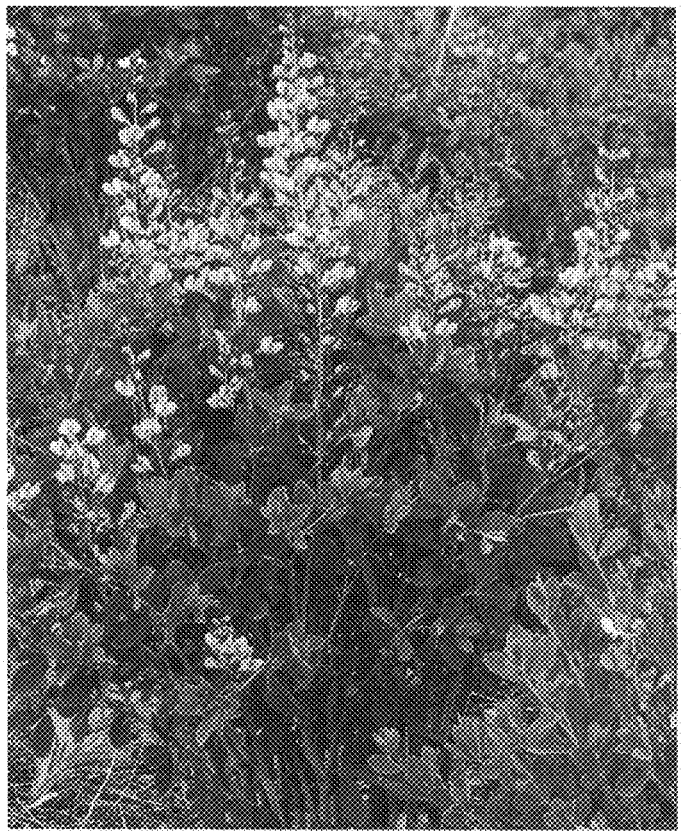
FIG. 2 shows the habit of a plant in full flower.

The following is a detailed description of 3 year-old plants of the new cultivar as grown outdoors in a trial plot at a wholesale nursery in Zeeland, Mich. Plants of the new cultivar have not been tested under all possible conditions. The phenotype may vary with changes in environment, climate, and cultural conditions without change however in the genotype. The color reference is in accordance with the 2001 edition of The Royal Horticultural Society Colour Chart except where general color dictionary terms are used.

Plant habit: Perennial, compact, well-branched, many-stemmed, vase-shaped growth habit with long inflorescences held above the foliage.

Plant size: About 100 cm tall from soil to top of flowers and 95 cm wide just below initial flowers;

Roots: Fibrous, well-branched, long, deeply rooted.

Root color: Nearest RHS 161D.

Growth and propagation:

*Propagation method*.—Stem cuttings, rooting in about three weeks; also can be propagated successfully by sterile plant tissue culture.

*Growth rate*.—Moderately, similar to other *Baptisia*.

Stems: Rigid and upright; highly glaucous; glabrous; cylindrical with longitudinal furrows; lower two to three nodes without leaves or branches; normally 20 to 25 stems per plant; main stem about 11.0 mm diameter at base and 100 cm tall to top of inflorescence, average about 90 cm tall and 10 mm diameter; normally about four alternately-arranged primary branches at 55 to 65 degree angle above horizontal, up to 35.0 cm long and 7.0 mm diameter, average for primary branches about 20.0 cm cm long and 6.0 mm diameter, smaller distally; and three alternately-arranged secondary branches per stem of about 18 cm long and 4.0 mm diameter, averaging about 16.0 cm long and 3.4mm diameter ; normally four alternately-arranged tertiary branches up to 16.0 cm long and 3.0 mm diameter, average about 10.0 cm long and 2.0 mm diameter.

Stem color: Base nearest RHS N138A without glaucous bloom and slightly more green than RHS 122D with glaucous bloom.

Stem scales: At stem nodes; slightly glaucous; dehiscing to leave behind thin scar; about 4.4 cm long and 18 mm wide at base and 23 mm wide in center; frequently with apical three leaflets about 4.0 mm long and 2.0 mm wide in center of retuse apex with sharply pointed sides; truncate base.

Stem scale color: Between RHS 138C and RHS 138B before dehiscing and nearest RHS N200A after dehiscing.

Internodes: Up to 13.0 cm apart between lowest branches, average about 8.0 cm.

Foliage: Alternate on stem; ternate to palmately compound with three leaflets; outer two leaflets at about 40 to 50 degree angle to middle leaflet; up to 5.0 cm long and 10.0 cm wide, average 3.8 cm long and 4.0 cm wide.

Leaflet: Three, oblanceolate; apex obtuse to rounded, base attenuate; margins entire; petiolate; top surface matte, scaberulose below; size up to 5.0 cm long and 2.1 cm wide, average about 3.8 cm long and 1.8 cm wide.

Leaflet color: Newly expanding between RHS N 144C and RHS 144B on upper and lower surfaces; mature upper and lower surface between RHS 139B and RHS N138B.

Venation: Pinnate, glabrous, thin, not conspicuous.

Vein color: Newly expanding foliage main center vein nearest RHS N144D above and nearest RHS 145D below; main center vein nearest RHS 139D above and lighter than RHS 142D or RHS 145D below; secondary veins same color as surrounding leaf tissue.

Petioles: Glabrous; slightly glaucous; concaved facing upward; up to about 1.2 cm long and 2.0 mm wide average 1.0 cm long and 1.5 mm wide.

Petiole color: Nearest 138A on upper and lower surfaces.

Stipules: Lanceolate, acute apex with base truncate to stem; up to 2.5 cm long and 12 mm wide, average 2.0 cm long and 10.0 mm wide with largest stipules below primary branches and decreasing distally and on secondary branches.

Stipule color: Nearest RHS 138A both surfaces.

Flower: Zygomorphic, papilionaceous, non-secund, held at about 40 degree angle above horizontal; beginning about 45 cm above soil; up to about 54 flowers per main raceme and about 34 per secondary branch; seasonally effective for about 3 to 4 weeks beginning in late May to early June in Zeeland, Mich. with about 36 flowers and 18 buds showing color during peak; individual flower remain effective and on raceme for about four days; individually about 2.4 cm long, 1.8 cm tall and 1.4 cm wide at tallest and widest portions; an upper banner, a lower keel made up of two lobes folded around gynoecium and androecium; and two lateral wings or alae laterally appressed against keel.

Flower fragrance: None detected.

Peduncle: Rounded with vertical ridges and furrows; glaucous; glabrous; from first flower to apex about 32 cm long; diameter at the base of first flower about 8.0 mm and about 2 mm diameter at the apex.

Peduncle color: Between RHS N138A and RHS 122A from glaucous covering; with tinting of nearest RHS N187A in upper portions, where exposed to higher light levels.

Pedicel: Round in cross section, glabrous, slightly glaucous; about 10.0 mm long and 1.0 mm diameter.

Pedicel color: Nearest RHS 146C with tinting of nearest RHS N187B in upper portions or where exposed to more light.

Calyx: Campanulate, five-lobed with top lobe only dissected about 1.0 mm and other lobes dissected about 3.0 mm deep, or four lobed with top lobe completely fused; compressed along petals; apex obtuse, base fused in basal two thirds; margins entire; slightly glaucous; about 9.0 mm long and 5.0 mm diameter; persists after petal drop.

Calyx color: Abaxial nearest RHS 138A with glaucous coating giving it a color of between RHS 122 B and RHS N138C; adaxial nearest RHS 144A.

Buds one day prior to anthesis: Oblong elliptic, flatted vertically; about 2.0 cm long and 11.0 mm tall and 6.0 mm wide.

Bud color: Three to four days prior to opening exposed banner petal margin between RHS 70A and RHS 70B, base of exposed banner petal lightening to between RHS 76D and RHS 77D exposed keel petal nearest RHS 10D and alae petals enclosed in banner petal; one day prior to opening exposed keel petal sides between RHS 76C and RHS 76D with darker veining nearest RHS N77D, dosal center spot of nearest RHS N77C with undertones of nearest RHS 200C, lighter lateral spot of nearest RHS 150D, exposed alae petals between RHS 70B and RHS 76A and exposed keel petal between RHS 11D and RHS 10D.

Petals: Five; with a lower fused keel, an upper banner, and two lateral wings or alae; keel comprised of two sections that are folded around stamens and pistil.

*Banner petal*.—Conduplicate, curved upward and backward and pinched in the middle; apex retuse, base claw-like, margin entire; about 1.8 cm long, 1.6 cm across at widest and 7.5 mm tall; young banner dorsal side color nearest RHS 75A at perimeter 1.0 mm margin with the inner center portion nearest RHS 76C with faint veining of nearest RHS 77B, center rib nearest RHS 150C with to darker blotches of about 4.0 mm on either side of the rib in center of petal of nearest RHS N77C; young ventral side apex RHS N77D lightening to between RHS 76C and RHS 76D with faint veining of nearest RHS N77C, base claw nearest RHS 145A with the middle of petal heavily speckled with tiny dots nearest RHS N77A and a light yellow section on middle perimeter of nearest RHS 11C; older banner petal shifting to closer to RHS N87D along center and margins of abaxial and adaxial surfaces with claw portion remaining unchanged.

*Keel*.—Comprised of two main lobes that are folded around stamens and pistil; fused in the distal one-third with the apex emarginate or retuse and the bases separate and claw-like; margin entire; top edge about one-third of the way from base has 2.0 mm smaller lobe pointing toward base; about 20 mm long 0.5 cm across and 9.0 mm tall with claw base narrowed to 1.0 mm wide for the proximal 5.0 mm; color of young and older outer keel sides between RHS 150D and RHS 1D with apex nearest RHS 2D on younger flower and RHS 3C on older flower with slight tinting of nearest RHS 163B; inner color same as outer color except main vein of older and younger flowers between RHS 145A and RHS 145B.

*Alae*.—Papilionaceous corolla appendage with rounded apex and claw-like base; with 2.0 mm lobe pointing toward base and about one-third of the way from base; about 21 mm long and 8.0 mm tall with the claw narrowed to 2.0 mm deep for the distal 5.0 mm; alae outside color nearest RHS 11D; color of lobe nearest RHS 11D on inside and outside of older and younger flowers, claw color nearest RHS 145C on inside and outside of older and younger flowers; blade color of younger flower nearest RHS N77B on upper half and lightening to lighter than RHS N80D in lower half of abaxial surface, and adaxial surface nearest RHS 77D on both upper and lower portions; blade color of older flower nearest RHS 85A on both abaxial and adaxial surfaces in upper and lower portions.

Receptacle: Disk-shaped, about 3.3 mm diameter and 1.2 mm depth; color nearest RHS 138A with tinting of RHS N187B.

Gynoecium: One, with superior ovary.

*Pistil*.—About 22.0 mm long and 1.5 mm wide.

*Style*.—Curved at tip, about 8.0 mm long and less than 1.0 mm diameter; color nearest RHS 145C.

*Stigma*.—Less than 0.5 mm diameter; color nearest RHS 145D.

*Ovary*.—Superior suspended by stipe; about 8 mm long and about 1.5 mm in diameter; color nearest RHS 144A.

*Stipe*.—About 7.0 mm long and 1.0 mm diameter; color nearest RHS 144B.

Androecium:

*Stamens*.—Ten, not united, about 20.0 mm long and 1.0 mm diameter.

*Filament*.—1.9 cm in length and less than 1 mm in diameter; slightly curved upward at tip; filament color between RHS 145D toward base and RHS 145C at distal region.

*Anther*.—Dorsifixed, oblong; about 2.0 mm long and 0.8 mm wide; color nearest RHS 15A. Pollen; spherical; abundant; color nearest RHS 15A.

Fruit and seeds: Have not yet been observed.

Hardiness: To USDA zones 4 to 8; heavy clay or light loamy sand soils; able to withstand drought conditions once established.

Diseases: Susceptibility or resistance to diseases beyond that typically found in other False Indigo plants has not been observed.

I claim:

1. A new and distinct cultivar of hardy herbaceous False Indigo plant named *Baptisia* 'Pink Truffles' as herein described and illustrated.

* * * * *